US008353967B2

(12) United States Patent
Malmquist et al.

(10) Patent No.: US 8,353,967 B2
(45) Date of Patent: Jan. 15, 2013

(54) SELF-SUPPORTING COLLAGEN TUNNEL FOR GUIDED TISSUE REGENERATION AND METHOD OF USING SAME

(75) Inventors: Jay Malmquist, Portland, OR (US); David Cheung, Arcadia, CA (US); William Knox, Newport Beach, CA (US)

(73) Assignee: Osseous Technologies of America, Newport Beach, CA (US)

( * ) Notice: Subject to any disclaimer, the term of this patent is extended or adjusted under 35 U.S.C. 154(b) by 296 days.

(21) Appl. No.: 12/853,793

(22) Filed: Aug. 10, 2010

(65) Prior Publication Data
US 2011/0035024 A1 Feb. 10, 2011

Related U.S. Application Data

(60) Provisional application No. 61/232,587, filed on Aug. 10, 2009, provisional application No. 61/329,934, filed on Apr. 30, 2010.

(51) Int. Cl.
*A61F 2/36* (2006.01)
(52) U.S. Cl. ............... 623/23.72; 623/17.17; 623/23.56; 623/23.62; 623/23.63; 424/93.7; 424/423; 424/549; 514/12
(58) Field of Classification Search .............. 623/17.17, 623/23.56, 23.62, 23.63; 424/93.7, 423, 424/549; 814/12
See application file for complete search history.

(56) References Cited

U.S. PATENT DOCUMENTS

| 3,422,181 | A | 1/1969 | Chirgwin, Jr. | |
|---|---|---|---|---|
| 4,059,899 | A | 11/1977 | Dyal | |
| 4,280,954 | A | 7/1981 | Yannas et al. | |
| 4,378,017 | A | 3/1983 | Kosugi et al. | |
| 4,657,548 | A | 4/1987 | Nichols | |
| 5,512,291 | A | 4/1996 | Li | |
| 5,997,896 | A | 12/1999 | Carr et al. | |
| 2005/0053638 | A1 | 3/2005 | Tanaka et al. | |
| 2005/0113930 | A1* | 5/2005 | Ganz et al. | 623/17.17 |
| 2007/0082021 | A1 | 4/2007 | Bates | |
| 2009/0265017 | A1* | 10/2009 | McKay | 623/23.63 |
| 2010/0215718 | A1* | 8/2010 | Swords et al. | 424/423 |

OTHER PUBLICATIONS

International Search Report dated Oct. 4, 2010 (Two (2) pages).
English Translation of International Preliminary Report on Patentability with Written Opinion dated Feb. 14, 2012, (seven (7) pages).

* cited by examiner

*Primary Examiner* — Vy Q Bui
(74) *Attorney, Agent, or Firm* — Crowell & Moring LLP

(57) ABSTRACT

A biocompatible, self-supporting, curved, collagen membrane adapted to be secured by bone tacks or bone screws over exposed bone at a desired bone graft site in the alveolar ridge of a patient such that the membrane defines a space having a predetermined height and width over the exposed bone, in which the membrane maintains its structural integrity for at least 4 months after implantation at the bone graft site and then naturally breaks down and is resorbed by the patient's body, a method of making such a membrane, and a method of using such a membrane for vertical augmentation of the alveolar ridge of the patient.

20 Claims, 2 Drawing Sheets

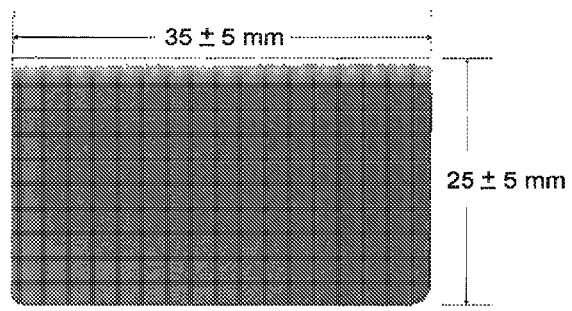
Fig. 2a
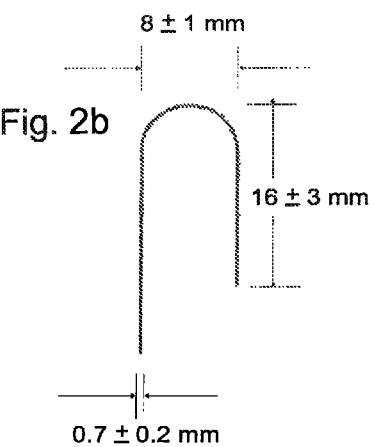
Fig. 2b
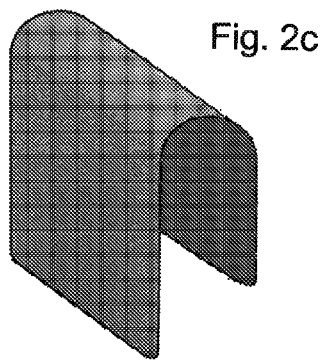
Fig. 2c
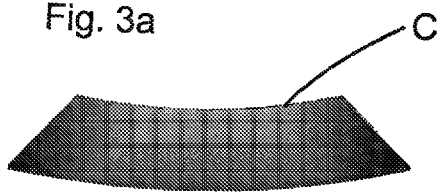
Fig. 3a
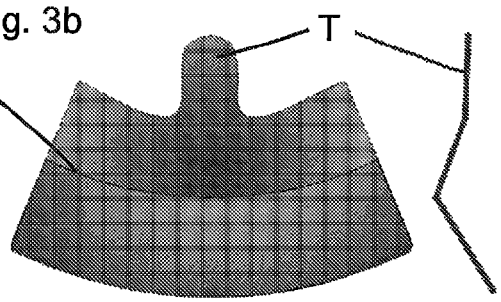
Fig. 3b
Fig. 3c

SELF-SUPPORTING COLLAGEN TUNNEL FOR GUIDED TISSUE REGENERATION AND METHOD OF USING SAME

FIELD OF THE INVENTION

The present invention relates to a self-supporting biphasic collagen membrane for guided tissue regeneration in a human or other mammal and to a method of using such a membrane in bone grafting, particularly in vertical augmentation of the alveolar ridge.

BACKGROUND OF THE INVENTION

Collagen has been used as an implantable biomaterial for more than 50 years. The collagen used for biomedical implants is either derived from animals (e.g., cows, pigs, horses) and humans, or it is manufactured in vitro using recombinant engineering. It is known to be biocompatible and is resorbed and remodeled like natural tissues, via cellular and enzymatic processes.

Conventional collagen implants typically have been made of highly porous, reconstituted bovine (i.e., cow) collagen. These collagen implants are commercially sold to surgeons as rectilinear sheets with uniform thicknesses and porosity. Their low density and high porosity make these collagen membranes supple and conformable. Unfortunately they therefore have inadequate tensile strength and stiffness, particularly after wetting with saline or blood, for use as a containment device in surgical applications.

Bone is the body's primarily structural tissue; consequently it can fracture and biomechanically fail. Fortunately, it has a remarkable ability to regenerate because bone tissue contains stem cells which are stimulated to form new bone within bone tissue and adjacent to the existing bone. Boney defects regenerate from stem cells residing in viable bone, stimulated by signally proteins, and multiplying on existing cells or on an extracellular matrix (i.e., trellis). Like all tissues, bone requires support via the vascular system to supply nutrients and cells, and to remove waste. Bone will not regenerate without prompt regeneration of new blood vessels (i.e., neovascularization), typically with the first days and weeks of the regenerative cascade.

After tooth loss, the adjacent jawbone (maxilla or mandible) frequently resorbs or atrophies. This may cause problems when it is desired to replace a missing tooth with a dental implant because the required depth of bone needed to adequately support the implant may not be present. Thus, prior to implanting a dental implant, it is often necessary for the oral surgeon to regenerate the adjacent bone to at least the minimum depth to provide adequate osseointegration of the dental implant. A common procedure for this purpose is alveolar ridge augmentation.

Various attempts have been made in the past to stimulate or augment bone regeneration by introducing a bone regenerating material proximate a deteriorated bone structure. Such efforts have met with limited success, however, because they have not been able adequately to control the placement of the bone regenerating material and thus guide the development of new or additional bone. Bone regenerating materials are classified as "bioactive" because they are biocompatible and stimulate new bone formation. Examples of bioactive materials are autograft, osteogenic stem cells, osteoinductive proteins, and osteoconductive matrices. Bioactive agents are typically delivered to the operative site by the surgeon as deformable, flowable biomaterials. The predictability of bioactive agents is poor, however because it is difficult to adequately control the placement of the bone regenerating material and thus guide the development of new or additional bone. Liquids, gels, granules, composites can be easily injected from syringes, but they can also go to unintended locations causing severe complications. Moreover, bioactive materials often migrate over time from the desired site. Measures undertaken to control the placement of the bone regenerating material may hinder cell ingrowth and formation of blood vessels needed for development of additional bone and thus impede the desired bone regeneration.

In alveolar ridge augmentation of atrophied jawbones to provide sufficient bone depth to facilitate stable implantation of a dental implant, a principal difficulty is the maintenance of the desired ridge shape, both as to height and as to width. While many answers exist for horizontal grafting, there are very few constructs to facilitate vertical grafting. In the past, bone graft material containment members constructed of titanium mesh have been used to address this problem. Titanium mesh is used because it has the requisite structural strength and integrity to provide containment and yet does not induce adverse effects in proximate tissues. However, because of its long term stability, it is necessary to carry out a second surgery to remove the containment member after the bone graft has achieved the desired degree of osseointegration before a dental implant can be implanted in the augmented bone. This results in concomitant tissue damage and often further delays the installation of the dental implant while the tissues damaged during removal of the titanium mesh containment member heal.

Thus, despite considerable efforts of the prior art, there has remained a long felt need for better methods of bone regeneration, especially for alveolar ridge augmentation in preparation for the installation of dental implants.

SUMMARY OF THE INVENTION

The present invention provides a self-supporting, arcuately curved sheet or tunnel of resorbable collagen which may be used by surgeons as an implantable medical device to aid in a variety of tissue regenerative indications. The self-supporting collagen tunnel provides resorbable biomaterial structure for containing or retaining cells, growth factors or particulate matrices for guided tissue regeneration or augmentation. The collagen tunnel of the present invention is particularly suitable for alveolar ridge augmentation, especially vertical alveolar ridge augmentation.

Assuring precise positioning of implanted tissue augmentation materials in a living body can be a difficult task. Moreover, because a living body is a dynamic environment, implanted materials may shift in position over time. The use of strategically shaped and implanted membranes according to the present invention, however, facilitates precise placement of implanted biomaterials and enables containment or retention of the implanted biomaterial at the desired location within the body.

The present invention makes use of collagen as a resorbable biomaterial for implantable medical devices to aid in tissue regeneration and repair.

Conventional highly porous implantable collagen membranes typically have been made of reconstituted, reticulated bovine (i.e., cow) collagen. Such materials are conventionally provided to surgeons as rectilinear sheets with uniform thicknesses of approximately 1 mm. Their low density and high porosity make such materials supple and conformable. Unfortunately, however, they therefore also have a low tensile strength and stiffness, particularly after wetting with saline or blood, and are inadequate for use as a containment device in surgical applications. Rather, they are difficult to handle and liable to tear themselves. In addition, such materials are difficult to retain in a desired position because they are so thin and fragile that they are difficult to attach at the desired location with a bone tack or suture.

Depending on the extent of cross linking, collagen biomaterials can be manufactured to resorb over a prescribed range, typically from 6 weeks to one year. For alveolar ridge augmentation, it is preferred that the collagen membrane of the tunnel be such that it maintains its shape and structural integrity for a period of from 4 to 6 months before breakdown and resorption occur.

The present invention uses collagen membranes with a curved or arcuately configured shape to facilitate tissue regeneration, particularly bone. This self-supporting curved shape is produced by casting collagen in an appropriately configured mold and lyophilizing, to form a porous collagen structure. The collagen membrane is then collapsed and cross linked to provide a self-supporting membranes of sufficient strength to function as a containment member for the required length of time.

The self-supporting collagen tunnels for guided tissue regeneration in accordance with the present invention may be produced by the following processes.

Collagen suitable for use in the containment members may be obtained by known techniques, for example, from bovine tendons. The collagen may be suitably purified for use by the process described in Nimni et al., U.S. Pat. No. 5,374,539, the entire disclosure of which is hereby incorporated herein by reference. The collagen fibers may also be treated for implantation by the process of Cheung, U.S. Pat. No. 7,008,763, the entire disclosure of which is likewise incorporated herein by reference.

The arcuately curved, self-supporting collagen membrane can be manufactured by a casting process using an appropriately shaped mold. The mold is filled with a collagen suspension. After lyphilization, the mold is opened and the membrane removed. The membrane can then be rehydrated and dried to provide a high strength three dimensional form.

The thickness of the curved, collagen membrane can be adjusted for biological, mechanical or intra-operative handling advantages. Thickness also can alter the resorption rate of the membrane. It can also alter the strength of the membrane, thus modifying the resistance to forces applied by the bioactive or bioinert materials forced into the device. Also, varying the thickness can assist the clinician to locate the device intra-operatively by facilitating handling. Because the thicker portions exhibit stronger mechanical properties, such as tensile strength or tear strength, due to its larger cross-sectional area, the collagen membrane containment member exhibits greatly improved resistance to tearing.

The thickness of the collagen membrane may range from about 0.3 mm to about 3 mm, preferably about 0.4 mm to about 2 mm, particularly preferably about 0.5 mm to 1.5 mm, and especially preferably from about 0.5 mm to 1 mm. The thickness of the resultant membrane can be modified by adjusting the gap between the mold surfaces of the mold in which it is formed.

If increased porosity is desired, macroscopic holes may be made in the membrane with strategically placed pins transecting the mold cavity. Alternatively, holes can be formed in the completed membrane with strategically placed pins, cuts or laser cutting. A third alternative is to use a selective rehydration/drying process in targeted areas of the membrane.

The self-sustaining, curved collagen containment member of the invention is malleable, by which is meant that the membrane can be folded to a desired shape or configuration and then will retain that configuration. This is achieved by bending the membrane beyond the elastic limit of the material and then creasing the membrane at the bending site. As a result, the membrane will retain its shape after being custom bent, intra-operatively by the surgeon.

The curved, collagen tunnel containment member of the invention is preferably distributed in a sterile package.

The self-sustaining collagen tunnel of the invention has a number of important advantages for guided tissue regeneration. It can be readily produced in lengths sufficient to contain a relatively long bone graft and can be readily trimmed to a desired length for shorter bone grafts. Thus, it is unnecessary to manufacture and maintain an inventory of different sized containment members for bone grafts of different lengths because a single standard size can be readily adapted to differing size requirements.

Because the collagen tunnel containment member of the invention is biocompatible and resorbable, it is unnecessary to perform a second surgery to remove the containment member after the bone graft has achieved a sufficient degree of osseointegration. Instead, the containment member of the invention can simply be left in place until it is naturally resorbed by the patient's body.

The self-supporting collagen tunnel of the invention also provides convenience for the surgeon who uses it. For example, if desired, a dental implant can be installed in a patient first without removing the collagen containment member or waiting for it to resorb. Instead, the implant may be successfully installed through the collagen tunnel containment member merely by making a small slit through the containment member at the desired implant location once the desired degree of osseointegration of the bone augmentation material has been achieved. Thus, scheduling flexibility is maximized and overall operating time for the surgeon and staff, as well as the patient, can be conserved by using the collagen tunnel containment member of the invention.

As used herein, the term "lyphilization" refers to "freeze drying" or vacuum drying.

In the process for producing the membranes of the invention, the a molded collagen suspension is placed in a freezer and then a vacuum is applied. Under vacuum, the water within the collagen moves directly from the solid phase to the gas phase. Consequently, there is no shrinking or change to the dimensions. This makes a highly porous, but relatively weak collagen structure. A key step in the production process according to the invention is then to lightly wet the porous collagen with water which collapses the porosity. The material is then air dried. This makes a much stronger/stiffer collagen membrane. Air drying also crosslinks some of the collagen molecules to further increase the strength and decrease the resorption rate.

BRIEF DESCRIPTION OF THE DRAWING

The invention will be described in further detail hereinafter with reference to illustrative examples of a preferred embodiments shown in the accompanying drawing figures, in which:

FIGS. 2a, 2b and 2c are, respectively, a side view, an end view and a perspective view of a second preferred embodiment of the collagen tunnel containment member of the invention designed specifically for posterior mandible applications; and FIGS. 3a, 3b and 3c are, respectively, a side view, a plan view and an end view of a third preferred embodiment of the collagen tunnel containment member of the invention designed specifically for anterior maxilla applications.

Figure 1:
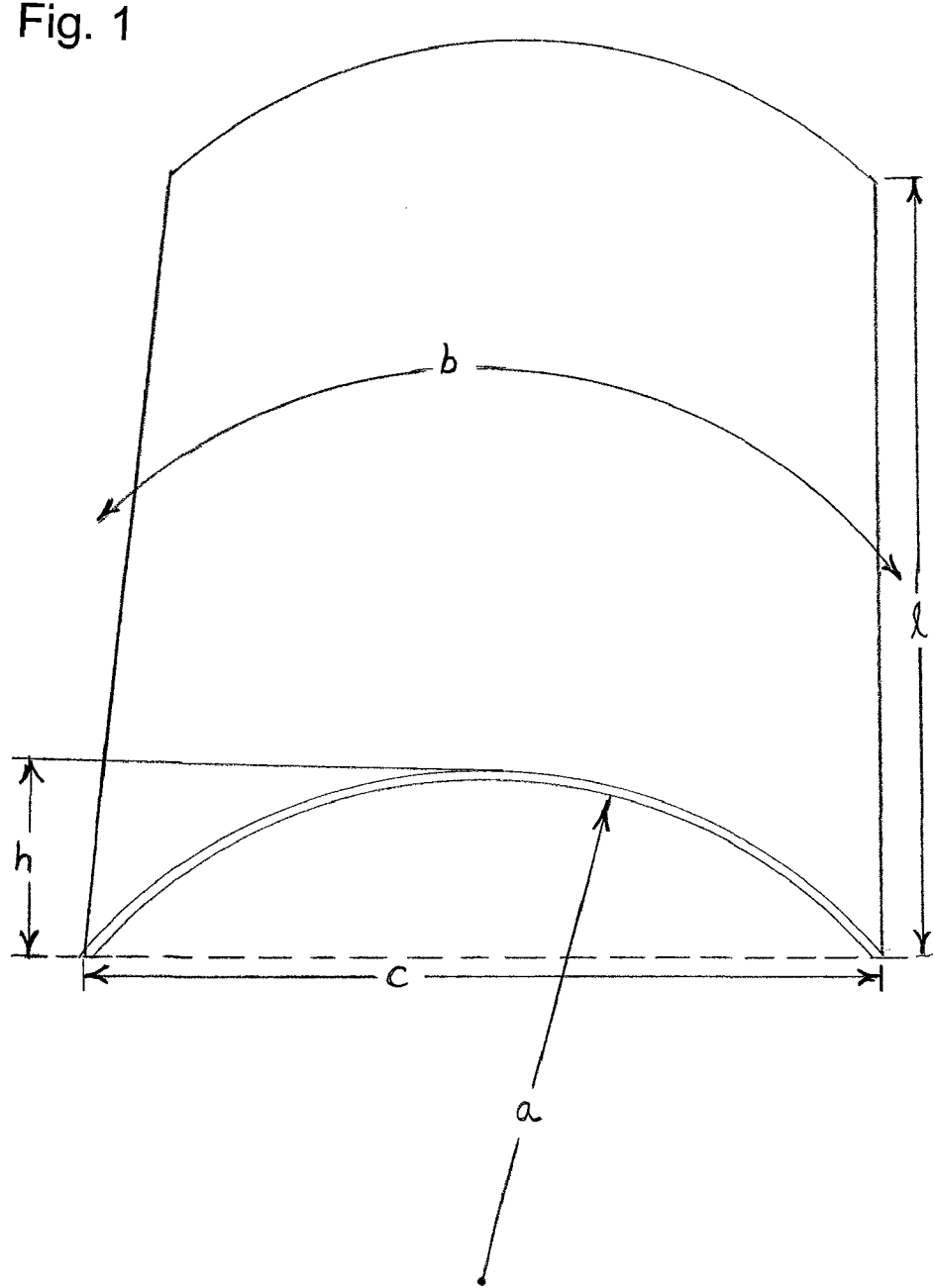
FIG. 1 is a schematic perspective representation of a first embodiment of a self-supporting collagen tunnel containment member according to the present invention.

It should be understood that these illustrations are only examples and that the collagen tunnel containment member of the invention may exist is a variety of configurations other than those shown in the drawings.

DETAILED DESCRIPTION OF THE INVENTION

FIG. 1 shows an illustrative collagen tunnel containment member according to the present invention. The containment member of the invention is comprised of single curved sheet of collagen having sufficient strength and structural integrity to be self-supporting. By "self-supporting" is meant that the collagen sheet must be sufficiently rigid that when the longitudinal edges of the curved collagen sheet are placed on a flat surface, it will not limply collapse against the surface, but instead will maintain its curved configuration with the central portion of the curved sheet elevated above the supporting surface.

However, the collagen sheet should not be absolutely rigid. Rather it is desirable for the collagen tunnel containment member to have sufficient flexibility that the oral surgeon can bend it to a desired configuration to fit the surgical installation site without cracking or creasing. After placement by the surgeon, the collagen tunnel can be held in the desired location by conventional bone tacks or bone screws.

As can be seen in FIG. 1, a preferred embodiment of the collagen tunnel membrane of the invention may have the configuration of a circumferential segment of an elongated tube such that the tube has a radially open face (see also FIGS. 2b and 2c). The collagen tunnel containment member of the invention typically may have a radius of curvature a in the range from about 5 to about 10 mm, an overall curved width b in the range from about 10 to about 25 mm, a tunnel width c in the range from about 10 to about 20 mm, a height h in the range from about 3 to about 8 mm and an overall length I in the range from about 10 to about 40 mm. Of course, the shape of the collagen tunnel can be varied in height and width allowing for various grafting needs. It is understood that the collagen tunnel may be readily trimmed using either scissors or a scalpel and/or bent to fit a desired installation site. In particular, it is understood that the collagen tunnel containment members will be manufactured in lengths longer than the length of a typical bone augmentation site and then trimmed to fit the site by the surgeon at the time of installation. In this way, it is possible to use a single size of collagen tunnel to fit various sized installation sites, and it is unnecessary to maintain an inventory of different sized containment members.

FIGS. 2a, 2b and 2c show another preferred embodiment of the collagen tunnel containment member of the invention. This embodiment is particularly designed for posterior mandible applications. The posterior mandible containment member takes the form of a sheet bent into a bight with two legs of uneven length joined by a curved center section. This design allows the containment member to be placed securely over the mandible, after which it can be securely tacked in place by placing bone tacks through one or both legs. The uneven lengths of the two legs allow the containment member to better fit the typical dimensions of the oral cavity adjacent the posterior mandible. The optimum dimensions of the containment member will necessarily vary depending on the size of the patient in whom the containment member is to be employed. However, in general the containment member may advantageously have an overall length of 35±5 mm; the two legs may have heights of 25±5 mm and 16±3 mm, respectively; and the spacing between the legs (i.e. the diameter of the curved section joining the two legs) may be about 8±1 mm. Moreover, the resorbable collagen material, from which the containment member is formed, can readily be trimmed to fit by the surgeon upon implantation. Then the tunnel or chamber formed under the curved center section between the containment member and the mandible can be filled as needed with bone augmentation material.

FIGS. 3a, 3b and 3c depict another especially advantageous embodiment of the containment member of the invention designed particularly for anterior maxilla applications. This embodiment takes the general form of a segment of a circle having a curvature that generally matches the curvature of the jaw of the patient in whom the containment member is to be employed. The containment member is bent or folded along a circumferential line "C" to form a peaked structure, best visualized in FIG. 3c. A tab "T" may be provided to facilitate handling of the containment member, as well as providing a securing site for insertion of a bone tack to fasten the containment member in place in a patient. In the illustrated embodiment, the tab is shown projecting radially inwardly from the center of the containment member, but persons skilled in the art will appreciate that such tabs could alternatively be located at other positions on the containment member. Likewise, only a single tab is shown, but persons skilled in the art will appreciate that more than one tab could be provided as needed. After the containment member is installed in a patient over the anterior maxilla, the resulting tunnel or chamber formed between the peaked portion of the containment member and the patient's maxilla can be packed as needed with bone augmentation material.

After installation of the collagen tunnel containment member at the desired surgical site, the tunnel is filled or packed with a suitable bone regeneration material, such as autograft, allograft, growth factors, or ceramic particles, for example apatite. Numerous such materials are well known in the art and are commercially available from various manufacturers. The collagen tunnel assures proper space maintenance and restrains the bone grafting material to exactly the correct location and configuration for maximum bone formation.

The capsule can be filled with bone graft material such as autograft, allograft, growth factors, or ceramic particles. The apical portion and lingual side are formed with a matrix of perforations which give these regions a high porosity for facilitating neovascular ingrowth. The buccal portion has high stiffness to retain the bone graft material crestally. As a result of this advantageous capsule structure, when the capsule is filled with bone regenerating material and properly inserted into the socket of an extracted tooth, the buccal plate is restored with regenerated bone to the height desired by the surgeon.

The self-supporting, curved, collagen tunnel containment members of the invention may be produced by the following casting process:

A 10-60 mg/ml suspension of purified collagen in 5-25% alcohol/water is formed. A particularly preferred suspension contains 15 mg of collagen per ml of a 10% solution of ethanol in water. The collagen fibers preferably have a native fibrous structure and a length of from 0.2 to 3 mm, particularly preferably about 1.5 mm. After removing air bubbles from the suspension, a fixed amount of the suspension is poured into a mold comprised of mating male and female mold members which form a curved mold cavity between them. The mold cavity is completely filled with the collagen suspension, and the main frame of the mold is tightly attached to the elastic surface of bottom plate.

The filled mold was then placed in −70° C. freezer. After solidification of the collagen matrix, one of the two vertical plates holding the frozen collagen was removed. The other vertical plate was also removed with the collagen on it. The plate with the frozen collagen was subsequently freeze-dried in a freeze-dryer.

The dried collagen was removed from the Freeze-dryer and sprayed with an alcohol solution. A preferred alcohol solution will contain 40 to 70% alcohol. A particularly preferred solution contains about 50% alcohol. The collagen material was then subjected to air drying followed by vacuum drying. The material was then heated at 100 to 140° C. for from 15 minutes to 2 hours. A preferred heat treatment is effected at 130° C. for 30 minutes. The heat treated collagen tunnel was then removed and cut to the desired size. The resulting material has a tensile strength of approximately 3600 g/mm² (35 MPa), a tensile modulus of approximately 95,000 g/mm² (932 MPa), pore diameters of less than 50 microns, and a porosity of less than 20%.

The thickness of the resorbable sheet material used to make the containment member of the invention may be varied, depending on circumstances, but typically the collagen material will have a thickness of about 0.7±0.2 mm.

The properties of the collagen structure may be varied to adjust the time frame for tissue break down and the loss of the structure of the geometric shape. Depending on the extent of cross-linking, collagen biomaterials can be manufactured to resorb over a prescribed period of time ranging from 6 weeks to a year or more. The rate of break down and resorption can also be varied by adjusting the thickness of the collagen membrane. Preferably, the collagen tunnel containment member of the invention will maintain its shape and structural integrity for a minimum of 4 months, especially preferably 4 to 6 months, to provide time for the bone graft material to integrate into the bone, after which time the collagen tunnel will break down naturally and be resorbed by the patient's body.

The self-supporting, curved collagen tunnel containment member of the present invention provides predictable space maintenance while at the same time being able to achieve ultimate biologic resorption (i.e., dissolution of the barrier) not heretofore available in the medical/dental grafting world. The collagen tunnel of the invention provides horizontal and vertical containment while promoting tissue healing using the unique properties of collagen. The collagen tunnel of the invention is capable of providing both graft containment and height and width space maintenance at the same time. The collagen fiber construction allows predictable breakdown of the geometric shape and maintains the desired geometry for the needed time frame of from four to six months so that the bone graft can mature and attain the strength to support the adjacent soft tissues and, ultimately, one or more dental implants.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A method of augmenting a bone in a patient, said method comprising:
   surgically exposing bone to be augmented at a desired bone graft site in the patient;
   disposing a resorbable self-supporting, curved, collagen membrane over the exposed bone at the desired bone graft site such that said collagen membrane provides a defined space of predetermined height and width adjacent the exposed bone; wherein the membrane retains its structural integrity for a desired time after installation at a bone graft site and then breaks down and is completely resorbed by the patient body;
   securing the collagen membrane in position with bone tacks or bone screws; and
   packing said defined space with a bone graft material.

2. A method as claimed in claim 1, wherein said collagen membrane is first trimmed to fit the bone graft site prior to being disposed over the exposed bone.

3. A method as claimed in claim 1, wherein the membrane retains its structural integrity for at least 4 months after installation at a bone graft site and then breaks down and is resorbed by the patient's body.

4. A method as claimed in claim 1, wherein the bone to be augmented is the alveolar ridge of the patient.

5. A method as claimed in claim 1, wherein the membrane is a biocompatible, collagen membrane adapted to be secured to the alveolar ridge of a bone graft patient for containing a bone graft material in a desired configuration and location on the alveolar ridge.

6. A method as claimed in claim 5, wherein the membrane retains its structural integrity for at least 4 months after installation at a bone graft site and then breaks down and is resorbed by the patient's body.

7. A method as claimed in claim 1, wherein the membrane has the configuration of an elongated tubular segment.

8. A method as claimed in claim 1, wherein the membrane is formed of collagen fibers having a native fibrous structure and a fiber length of from 0.2 to 3 millimeters.

9. A method as claimed in claim 8, wherein said fibers have an average length of about 1.5 millimeters.

10. A method as claimed in claim 1, wherein said collagen membrane has a tensile strength of approximately 3600 g/mm², a tensile modulus of approximately 95,000 g/mm², pore diameters of less than 50 microns, and a porosity of less than 20%.

11. A method as claimed in claim 1, wherein said membrane has a radius of curvature a in the range from about 5 to about 10 mm, an overall curved width b in the range from about 10 to about 25 mm, a tunnel width c in the range from about 10 to about 20 mm, a height h in the range from about 3 to about 8 mm and an overall length l in the range from about 10 to about 40 mm.

12. A method as claimed in claim 1, wherein said membrane is a resorbable collagen membrane produced by the process comprising:
   forming a suspension of collagen fibers in an alcohol/water solution;
   pouring the suspension into a curved mold cavity of a mold;
   subjecting the mold to freezing temperature until the suspension in the mold solidifies;
   opening the mold;
   subjecting the frozen suspension to freeze drying to produce a membrane;
   spraying the freeze-dried membrane with an alcohol/water solution;
   thereafter subjecting the membrane to drying; and
   heat treating the dried membrane.

13. A method as claimed in claim 12, wherein said suspension contains from 10 to 60 mg/ml of collagen fibers having a length of 0.2 to 3 mm in a 5 to 25% solution of alcohol in water.

14. A method as claimed in claim 12, wherein the membrane is sprayed with an alcohol/water solution containing from 40 to 70% alcohol.

15. A method as claimed in claim 12, wherein perforations are formed in the membrane during casting by extending a plurality of pins through the mold in which the membrane is formed.

16. A method as claimed in claim 12, wherein the heat treatment is effected at a temperature of from 100 to 140° C. for a period of from 15 minutes to 2 hours.

17. A method as claimed in claim 1, wherein said membrane takes the form of a bight formed with two legs of unequal length joined by a curved center section.

18. A method as claimed in claim 17, wherein the two legs are spaced apart a distance of about 8±1 mm.

19. A method as claimed in claim 1, wherein said membrane takes the form of a circular segment with a circumferential fold forming a peaked structure.

20. A method as claimed in claim 19, wherein said membrane is provided with at least one projecting tab.

* * * * *